US010441145B2

(12) United States Patent
Kugimiya et al.

(10) Patent No.: US 10,441,145 B2
(45) Date of Patent: Oct. 15, 2019

(54) ENDOSCOPE SYSTEM

(71) Applicant: OLYMPUS CORPORATION, Tokyo (JP)

(72) Inventors: Hideyuki Kugimiya, Hachioji (JP); Ryo Koshida, Fuchu (JP); Takehiko Ito, Hidaka (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 15/628,969

(22) Filed: Jun. 21, 2017

(65) Prior Publication Data

US 2017/0280982 A1 Oct. 5, 2017

Related U.S. Application Data

(63) Continuation of application No. PCT/JP2016/076087, filed on Sep. 6, 2016.

(30) Foreign Application Priority Data

Mar. 3, 2016 (JP) ................................ 2016-041250

(51) Int. Cl.
*A61B 1/04* (2006.01)
*A61B 1/00* (2006.01)
(Continued)

(52) U.S. Cl.
CPC ............ *A61B 1/04* (2013.01); *A61B 1/00009* (2013.01); *A61B 1/00013* (2013.01);
(Continued)

(58) Field of Classification Search
CPC .. G02B 23/2415; G02B 23/2484; H04N 7/22; A61B 1/00009; A61B 1/00011;
(Continued)

(56) References Cited

U.S. PATENT DOCUMENTS 4,884,134 A * 11/1989 Tsuji ........................ A61B 1/05 348/73
5,374,953 A * 12/1994 Sasaki ...................... A61B 1/05 348/65

(Continued)

FOREIGN PATENT DOCUMENTS

EP 2954835 A1 12/2015
JP 2015-134039 A 7/2015

(Continued)

*Primary Examiner* — Aaron B Fairchild
(74) *Attorney, Agent, or Firm* — Scully Scott Murphy & Presser, P.C.

(57) ABSTRACT

An endoscope system includes an image pickup portion configured to pick up an image of a subject and output the image as an electrical signal, a processor configured to perform, on the electrical signal, a signal correction that converts the electrical signal into a signal of a video format that is compatible with a signal processed by the image processing apparatus, and an image processing portion configured to perform image processing on the electrical signal after the signal correction. An E/O converter that converts the electrical signal into an optical signal, an optical fiber that transmits the optical signal, and an O/E converter that converts the optical signal into the electrical signal, are arranged in at least one of between the image pickup portion and the processor, and between the processor and the image processing portion.

8 Claims, 11 Drawing Sheets

(51) Int. Cl.
*G02B 23/24* (2006.01)
*H04N 5/232* (2006.01)
*A61B 1/045* (2006.01)
*H04N 5/225* (2006.01)

(52) U.S. Cl.
CPC .......... *A61B 1/045* (2013.01); *G02B 23/2484* (2013.01); *H04N 5/23203* (2013.01); *A61B 1/00011* (2013.01); *G02B 23/2415* (2013.01); *H04N 2005/2255* (2013.01)

(58) Field of Classification Search
CPC ... A61B 1/04; A61B 1/00006; A61B 1/00013; A61B 1/00018; A61B 1/045; A61B 1/05; A61B 1/051
See application file for complete search history.

(56) References Cited

U.S. PATENT DOCUMENTS

| | | | | |
|---|---|---|---|---|
| 2002/0126204 | A1* | 9/2002 | Takeshige .......... | A61B 1/00009 348/74 |
| 2013/0235175 | A1 | 9/2013 | Kazama | |
| 2015/0112135 | A1* | 4/2015 | Hirota ................ | A61B 1/00009 600/109 |
| 2015/0335230 | A1 | 11/2015 | Tomatsu | |
| 2016/0206185 | A1 | 7/2016 | Kinouchi | |

FOREIGN PATENT DOCUMENTS

| | | | |
|---|---|---|---|
| JP | 5869194 | B2 | 2/2016 |
| WO | WO 2012/046856 | A1 | 4/2012 |
| WO | WO 2016/002415 | A1 | 1/2016 |

* cited by examiner

FIG. 8

| COMBINATION NUMBER | ENDOSCOPE | FIRST CABLE | INPUT MODULE | SECOND CABLE | CONTROL MODULE |
|---|---|---|---|---|---|
| (1) | A1 | X2 | B2 | X2 | C2 |
| (2) | A1 | X2 | B2 | X4 | C1 |
| (3) | A1 | X2 | B4 | X1 | C2 |
| (4) | A1 | X2 | B4 | X3 | C1 |
| (5) | A1 | X2 | B4 | X5 | C2 |
| (6) | A1 | X4 | B1 | X2 | C2 |
| (7) | A1 | X4 | B1 | X4 | C1 |
| (8) | A1 | X4 | B3 | X1 | C2 |
| (9) | A1 | X4 | B3 | X3 | C1 |
| (10) | A1 | X4 | B3 | X5 | C2 |
| (11) | A2 | X1 | B2 | X2 | C2 |
| (12) | A2 | X1 | B2 | X4 | C1 |
| (13) | A2 | X1 | B4 | X1 | C2 |
| (14) | A2 | X1 | B4 | X3 | C1 |
| (15) | A2 | X1 | B4 | X5 | C2 |
| (16) | A2 | X3 | B1 | X2 | C2 |
| (17) | A2 | X3 | B1 | X4 | C1 |
| (18) | A2 | X3 | B3 | X1 | C2 |
| (19) | A2 | X3 | B3 | X3 | C1 |
| (20) | A2 | X3 | B3 | X5 | C2 |
| (21) | A2 | X5 | B2 | X2 | C2 |
| (22) | A2 | X5 | B2 | X4 | C1 |
| (23) | A2 | X5 | B4 | X1 | C2 |
| (24) | A2 | X5 | B4 | X3 | C1 |
| N/A | A2 | X5 | B4 | X5 | C2 |

ENDOSCOPE SYSTEM

CROSS REFERENCE TO RELATED APPLICATION

This application is a continuation application of PCT/JP2016/076087 filed on Sep. 6, 2016 and claims benefit of Japanese Application No. 2016-041250 filed in Japan on Mar. 3, 2016, the entire contents of which are incorporated herein by this reference.

BACKGROUND OF INVENTION

1. Field of the Invention

The present invention relates to an endoscope system that includes an image pickup apparatus, a processor, and an image processing apparatus that generates a video signal.

2. Description of the Related Art

An endoscope that functions as an image pickup apparatus is provided with an elongated insertion portion that acquires an optical image at a distal end portion. Also, an inside of a subject which cannot be observed from the outside can be observed as an endoscopic image by inserting the insertion portion into the subject.

In particular, with an electronic endoscope, an optical image of a subject is photoelectrically converted using an image pickup device or the like, and transmitted to an image processing apparatus as an electrical signal. After being processed by the image processing apparatus, the optical image is displayed as an endoscopic image on a display unit such as a monitor and observed.

With an endoscope system using such an electronic endoscope, a higher definition endoscopic image is required to perform a more reliable determination and treatment.

An endoscope system is proposed that converts an electrical image pickup signal into an optical signal, transmits the optical signal using optical fiber instead of transmitting an electrical signal using a metal conducting wire because the amount of data of the image pickup signal of a high definition endoscopic image is large, and then converts the transmitted optical signal back into an electrical image pickup signal and perfoims image processing and the like.

For example, International Publication No. WO 2012/46856 describes an endoscope system that includes an electric cable and a fiber optic cable that transmit pixel infoiiiiation outputted by an light receiving portion, an image processing portion that generates an image on the basis of the pixel information transmitted from the fiber optic cable or the pixel information transmitted from the electric cable, and a control portion that displays the image generated by the image generating portion on a display unit and determines whether there is a transmission anomaly in the fiber optic cable, and selects, as the pixel information to be processed by the image processing portion, one of the pixel information transmitted from the fiber optic cable and the pixel information transmitted from the electric cable, in accordance with whether there is a transmission anomaly in the fiber optic cable.

SUMMARY OF THE INVENTION

An endoscope system according to an aspect of the present invention includes an image pickup apparatus configured to pick up an image of a subject and output the image as an electrical signal; a processor configured to perform a predetermined signal correction on the electrical signal outputted from the image pickup apparatus and output the electrical signal; and an image processing apparatus configured to perform image processing on the electrical signal after the signal correction, which is outputted from the processor, and generate a video signal, wherein the processor performs, as the predetermined signal correction, processing that converts a signal into a signal of a video format that is compatible with a signal processed by the image processing apparatus, and an electrical-to-optical converter configured to convert the electrical signal into an optical signal, an optical transmitting member configured to transmit the optical signal converted by the electrical-to-optical converter, and an optical-to-electrical converter configured to convert the optical signal transmitted by the optical transmitting member into the electrical signal, are arranged in at least one of between the image pickup apparatus and the processor, and between the processor and the image processing apparatus.

BRIEF DESCRIPTION OF THE DRAWINGS

FIG. 8 is a chart showing combinations when the endoscopes and the control modules are connected by cables via the input modules, according to the first embodiment;

DETAILED DESCRIPTION OF THE PREFERRED EMBODIMENT(S)

Hereinafter, a mode for carrying out the present invention will be described with reference to the drawings.

[First Embodiment]

Figure 1:
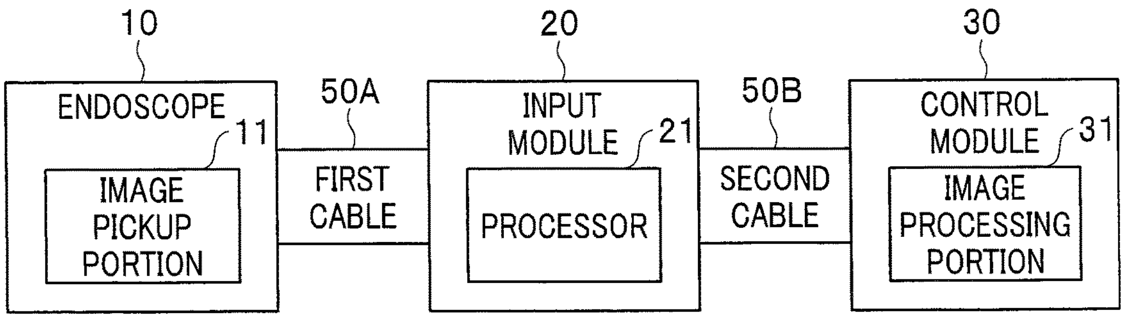
FIG. 1 is a view showing the basic configuration of an endoscope system according to a first embodiment of the present invention.

FIG. 1 to FIG. 10 illustrate a first embodiment of the present invention. FIG. 1 is a view showing the basic configuration of an endoscope system.

As shown in FIG. 1, the endoscope system includes an endoscope 10, an input module 20, a control module 30, a first cable 50A that connects the endoscope 10 to the input module 20, and a second cable 50B that connects the input module 20 to the control module 30.

The endoscope 10 includes an image pickup portion 11 configured to pick up an image of a subject and output the image as an electrical signal.

The input module 20 is also referred to as a relay substrate, and includes a processor 21 configured to perform a predetermined signal correction on the electrical signal outputted from the image pickup portion 11, and output the corrected electrical signal.

The control module 30 is also referred to as a signal processing apparatus, and includes an image processing portion 31 configured to perform image processing on the electrical signal after the signal correction, which has been outputted from the processor 21, and generate a video signal.

The first cable 50A is detachably connected at one end to the endoscope 10, and is detachably connected at the other end to the input module 20, and is designed to transmit a signal between the endoscope 10 and the input module 20.

The second cable 50B is detachably connected at one end to the input module 20, and is detachably connected at the other end to the control module 30, and is designed to transmit a signal between the input module 20 and the control module 30.

Also, with this endoscope system, an electrical-to-optical converter (more specifically, an E/O converter 51 that will be described later) that converts an electrical signal into an optical signal, an optical transmitting member (more specifically, optical fiber 52 that will be described later) that transmits the optical signal converted by the electrical-to-optical converter, and an optical-to-electrical converter (more specifically, an O/E converter 53 that will be described later) that converts the optical signal transmitted by the optical transmitting member into an electrical signal, are arranged in at least one of between the image pickup portion 11 and the processor 21, and between the processor 21 and the image processing portion 31.

That is, the optical transmitting member that transmits the optical signal is arranged in at least one of the first cable 50A and the second cable 50B.

The image pickup portion 11 includes a light receiving portion 12 (see FIG. 9 and the like) that is an image pickup apparatus configured as a CMOS image pickup device, for example, and receives reflected light from the subject and performs photoelectric conversion. The output of the image pickup signal from the light receiving portion 12 will be described with reference to FIG. 2 and FIG. 3.

Figure 2:
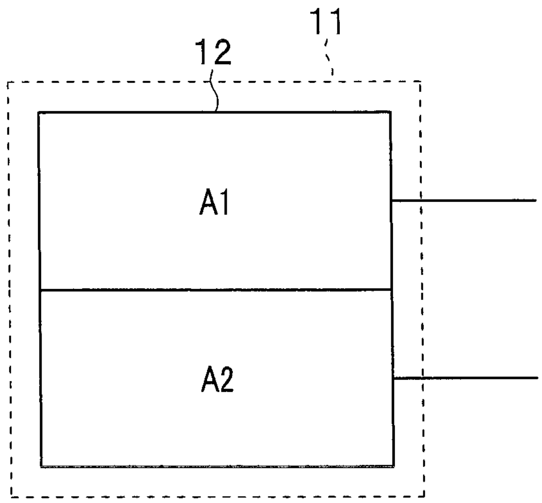
FIG. 2 is a view of an example in which there are two lines outputted from a light receiving portion, according to the first embodiment.
Figure 3:
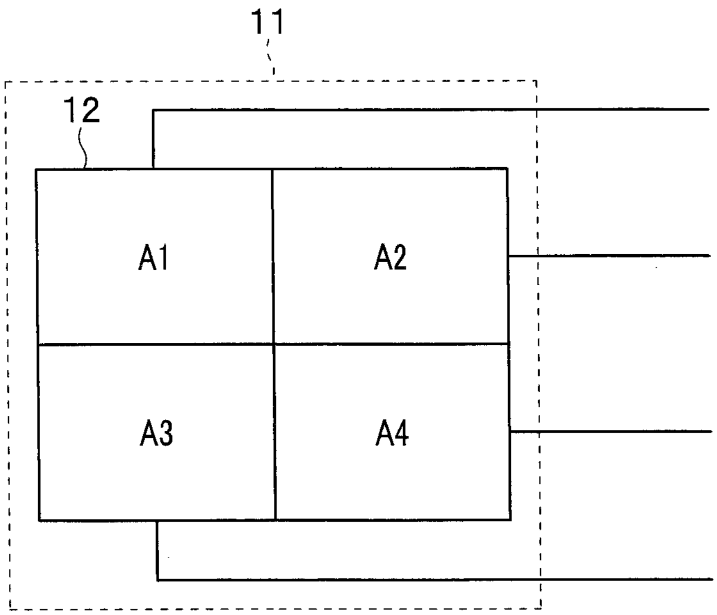
FIG. 3 is a view of an example in which there are four lines outputted from a light receiving portion, according to the first embodiment.

Here, FIG. 2 is a view of an example in which there are two lines outputted from the light receiving portion 12, and FIG. 3 is a view of an example in which there are four lines outputted from the light receiving portion 12.

The image pickup portion 11 of the present embodiment is configured to pick up an image of the subject, and output the image as a digital signal of a plurality of lines. More specifically, the light receiving portion 12 is divided into a plurality of image pickup areas, and the image pickup portion 11 outputs an image pickup signal as a different line for each image pickup area.

In the example shown in FIG. 2, the light receiving portion 12 is divided into two, i.e., a first image pickup area A1 and a second image pickup area A2, and the image pickup signal from each of the image pickup areas A1, A2 is outputted as a different line.

Also, in the example shown in FIG. 3, the light receiving portion 12 is divided into four, i.e., first to fourth image pickup areas A1 to A4, and the image pickup signal from each of the image pickup areas A1, A4 is outputted as a different line.

Note that it is not essential that the image pickup area be divided, but dividing the image pickup area is advantageous in that it improves the transmission speed of information due to the information being outputted over a plurality of lines.

Also, when dividing the image pickup area, the number of divisions may be an appropriate number of two or more, and the method of dividing the image pickup area is not limited to a method that divides the image pickup area by local region as shown in FIG. 2 and FIG. 3. As an example, a dividing method in which, when n is a natural number, all of (2n−1) lines that are odd-numbered lines are set to a first image pickup area, and all of 2n lines that are even-numbered lines are set to a second image pickup area, may be employed.

In the present embodiment, a case in which two lines of output, as shown in FIG. 2, is employed will be described as an example.

Figure 4:
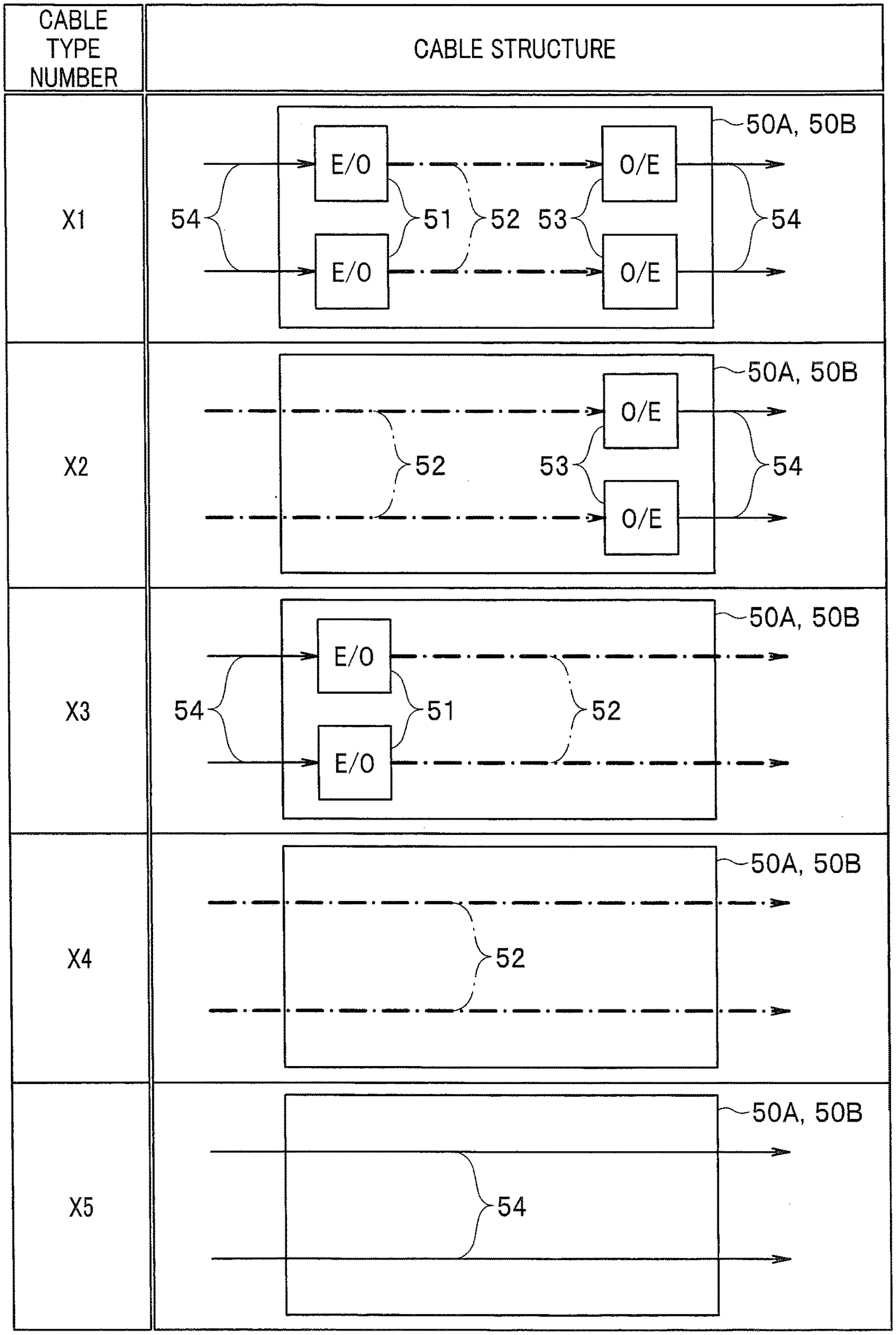
FIG. 4 is a chart showing different types of cables according to the first embodiment.

FIG. 4 is a chart illustrating different types of cables. The different types of cables shown in FIG. 4 can be applied to both the first cable 50A and the second cable 50B. Note that FIG. 4 to FIG. 7 schematically show the components when at least a portion of a signal transmission path from the endoscope 10 to the control module 30 via the input module 20 pertains to an optical signal. The rest of the components, which are typical components (for example, a metal wire 55 shown in FIG. 9), is not shown.

Note that because the image pickup signal is transmitted from the endoscope 10 to the control module 30 via the input module 20, the endoscope 10 side is an upstream side of the transmission path of the image pickup signal, and the control module 30 side is a downstream side. Therefore, in FIG. 4 to FIG. 7 that will be described later, the left side is the upstream side, and the right side is the downstream side, in accordance with FIG. 1.

A cable X1 includes two lines of optical fiber 52 that is an optical transmitting member, respectively corresponding to the two lines outputted from the light receiving portion 12, and transmits an optical signal. Furthermore, the electrical-to-optical converter (E/O converter) 51 is provided on the upstream side (the upstream end of the optical fiber 52) in the cable X1, and the optical-to-electrical converter (O/E converter) 53 is provided on the downstream side (the downstream end of the optical fiber 52) in the cable X1.

Here, the E/O converter 51 includes, for example, a light-emitting device and a light-emitting device driving portion, and generates and outputs an optical signal by the light-emitting device driving portion driving the light-emitting device in accordance with an electrical signal that is inputted. Also, the O/E converter 53 includes, for example, a photodiode that converts an optical signal into a current signal, and a transimpedance amplifier that converts a current signal into a voltage signal. The O/E converter 53 converts the inputted optical signal into an electrical signal, and outputs the electrical signal.

Therefore, the cable X1 is configured to receive an electrical signal from a metal wire 54 that is a metal transmitting member, convert the electrical signal into an optical signal by the E/O converter 51, transmit the converted optical signal through the optical fiber 52, convert the optical signal transmitted through the optical fiber 52 into an electrical signal by the O/E converter 53, and transmit the converted electrical signal to the metal wire 54. That is, the cable X1 performs electrical-to-optical conversion, optical signal transmission, and optical-to-electrical conversion, with the input and the output being electrical signals.

Next, a cable X2 includes two lines of the optical fiber 52, and the O/E converter 53 is provided on the downstream side (the downstream end of the optical fiber 52) in the cable X2. Also, the cable X2 performs optical signal transmission and optical-to-electrical conversion, with the input being an optical signal, and the output being an electrical signal.

The cable X3 includes two lines of the optical fiber 52, and the E/O converter 51 is provided on the upstream side (the upstream end of the optical fiber 52) in the cable X3. Also, the cable X3 performs electrical-to-optical conversion and optical signal transmission, with the input being an electrical signal, and the output being an optical signal.

The cable X4 includes two lines of the optical fiber 52. Also, the cable X4 performs optical signal transmission, with the input and the output being optical signals.

The cable X5 includes two lines of the metal wire 54. Also, the cable X5 performs electrical signal transmission, with the input and the output being electrical signals.

Figure 5:
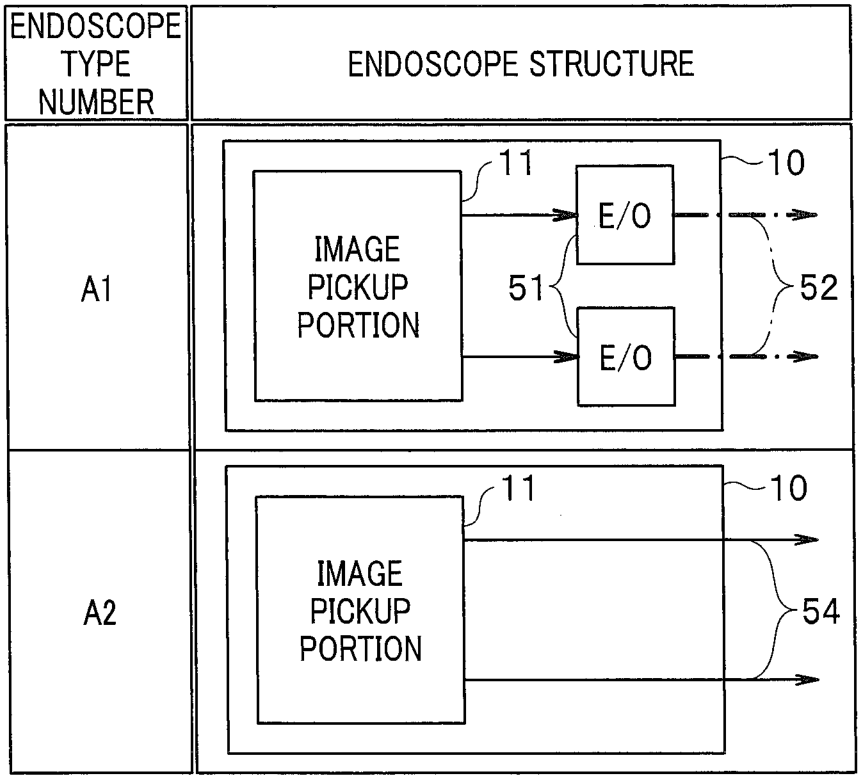
FIG. 5 is a chart showing different types of endoscopes according to the first embodiment.

Next, FIG. 5 is a chart showing different types of endoscopes 10.

An endoscope A1 is internally provided with the E/O converter 51 for each output line, and electrooptically converts the electrical signal outputted from the image pickup portion 11 by the E/O converter 51, and then outputs the resultant optical signal to the optical fiber 52. Therefore, the output of the endoscope A1 is an optical signal.

An endoscope A2 is not equipped with the E/O converter 51, and outputs the electrical signal outputted from the image pickup portion 11 to the metal wire 54. That is, the output of the endoscope A2 is an electrical signal.

Figure 6:
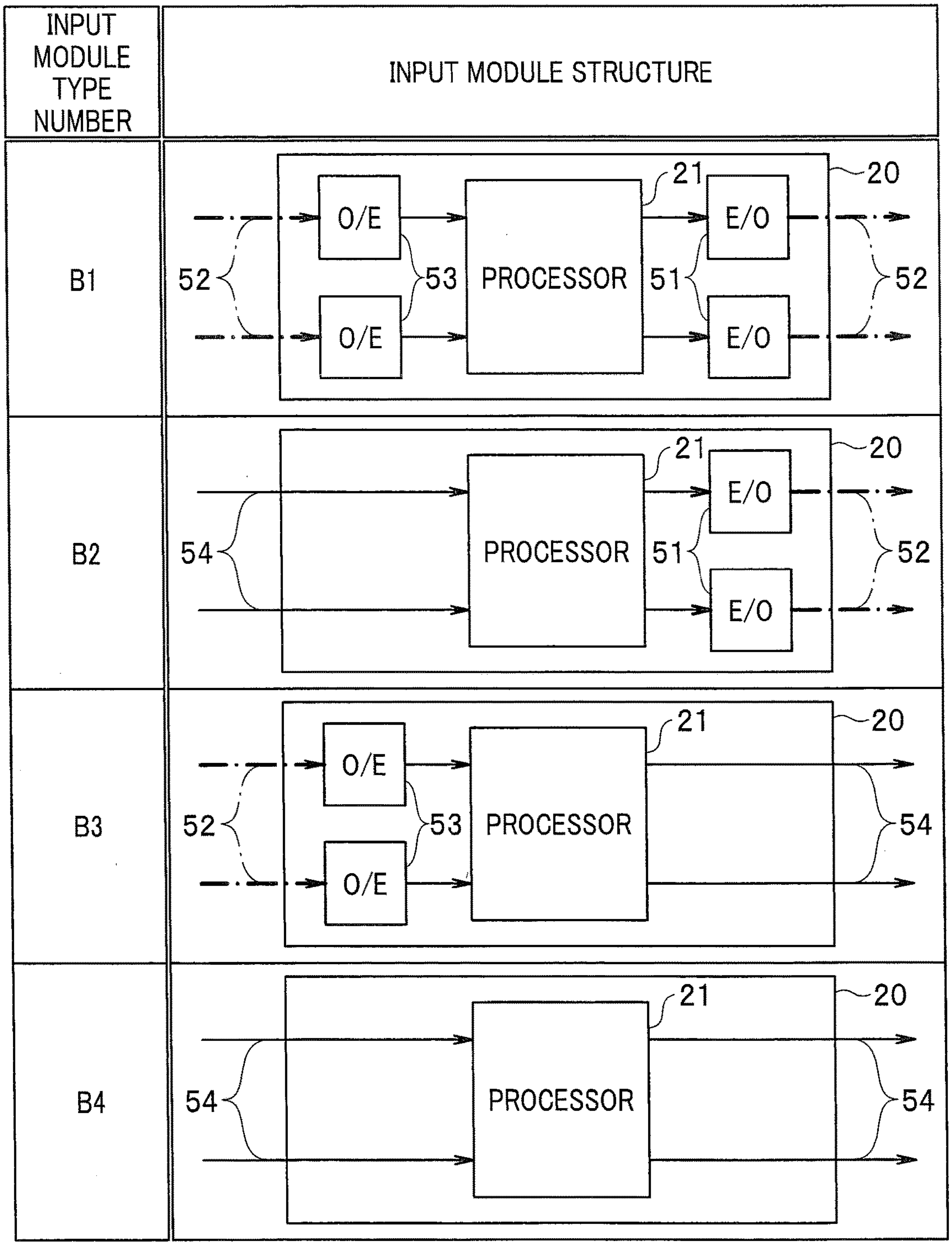
FIG. 6 is a chart showing different types of input modules according to the first embodiment.

Continuing on, FIG. 6 is a chart showing different types of input modules 20.

An input module B1 is internally provided with the O/E converter 53 on the upstream side of the processor 21, and is internally provided with the E/O converter 51 on the downstream side of the processor 21. The input and the output are optical signals.

An input module B2 is internally provided with the E/O converter 51 on the downstream side of the processor 21. The input is an electrical signal, and the output is an optical signal.

An input module B3 is internally provided with the O/E converter 53 on the upstream side of the processor 21. The input is an optical signal, and the output is an electrical signal.

An input module B4 is not provided with either the E/O converter 51 or the O/E converter 53. The input and the output are electrical signals.

Figure 7:
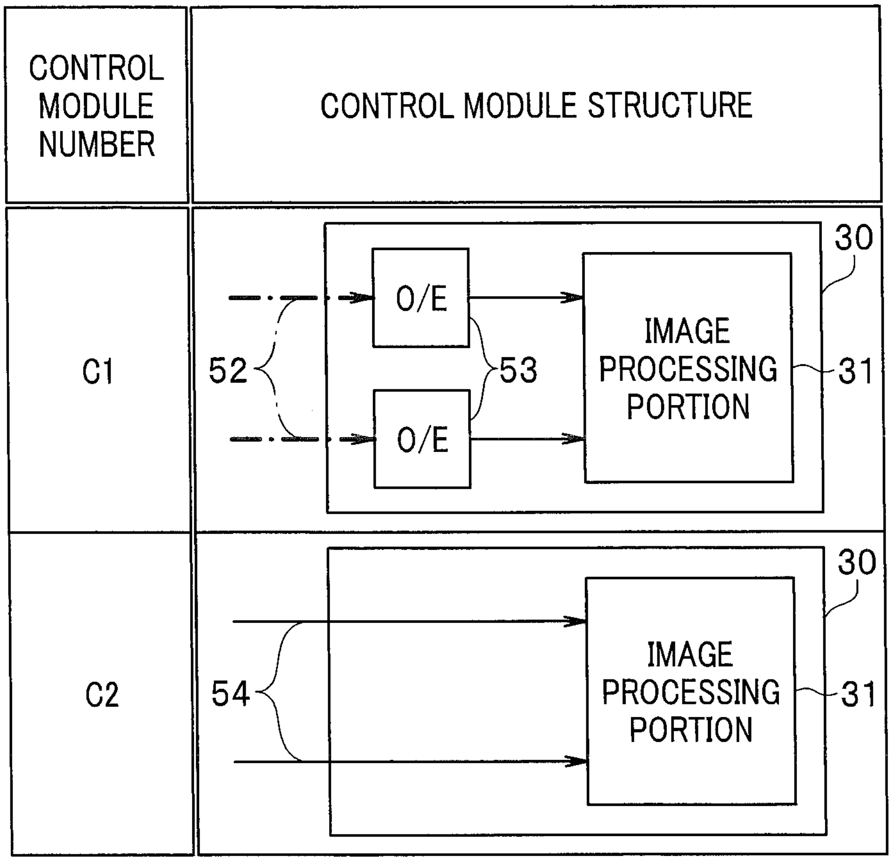
FIG. 7 is a chart showing different types of control modules according to the first embodiment.

FIG. 7 is a chart showing different types of control modules 30.

A control module C1 is internally provided with the O/E converter 53, and photoelectrically converts the optical signal received via the optical fiber 52 by the O/E converter 53, and then inputs the resultant electrical signal to the image processing portion 31. Therefore, the input of the control module C1 is an optical signal.

A control module C2 is not provided with the O/E converter 53, and inputs the electrical signal transmitted through the metal wire 54 to the image processing portion 31. That is, the input of the control module C2 is an electrical signal.

The possible combinations of the different types of endoscopes 10, first cables 50A, input modules 20, second cables 50B, and control modules 30 as shown in FIG. 4 to FIG. 7 are as shown in FIG. 8. Here, FIG. 8 is a chart showing combinations when the endoscopes 10 and the control modules 30 are connected by the cables 50A and 50B via the input modules 20.

For example, when the endoscope 10 is the endoscope A1, the output is an optical signal, so for the first cable 50A, only the cables X2 and X4 in which the input is an optical signal can be connected. The cables X1, X3, and X5 in which the input is an electrical signal cannot be connected.

On the other hand, when the endoscope 10 is the endoscope A2, the output is an electrical signal, so for the first cable 50A, only the cables X1, X3, and X5 in which the input is an electrical signal can be connected. The cables X2 and X4 in which the input is an optical signal cannot be connected.

In this way, the output signal of the endoscope 10 and the input signal of the first cable 50A must match in terms of the type of optical/electrical signal.

Similarly, the output signal of the first cable 50A and the input signal of the input module 20, the output signal of the input module 20 and the input signal of the second cable 50B, and the output signal of the second cable 50B and the input signal of the control module 30 must respectively match in terms of the type of optical/electrical signal.

The chart of FIG. 8 shows the possible combinations under this kind of limitation.

Once the type of the first cable 50A and the type of the second cable 50B shown in FIG. 4 are determined, the type of the endoscope 10 shown in FIG. 5, the type of the input module 20 shown in FIG. 6, and the type of the control module 30 shown in FIG. 7 are then respectively uniquely determined.

Therefore, the number of possible combinations is 5×5=25, because there are five types of the first cable 50A, i.e., X1 to X5, and five types of the second cable 50B, i.e., X1 to X5.

However, in the present embodiment, it is presupposed that an optical transmitting member that transmits an optical signal is arranged in at least one of the first cable 50A and the second cable 50B. Therefore, a configuration in which the cable X5 that transmits an electrical signal is arranged in both the first cable 50A and the second cable 50B, in the bottom row of the chart in FIG. 8, does not apply to the configuration of the present embodiment, so N/A is written in for the combination number.

Therefore, there are 24 possible combinations, i.e., (1) to (24), in the present embodiment, as shown in FIG. 8.

For example, when any one of the cables X1 to X4 is used for the first cable 50A (with combination numbers (1) to (20)), the first cable 50A includes the optical fiber 52. At this time, the E/O converter 51 is arranged in the endoscope 10, or on the endoscope 10 side of the optical fiber 52 in the first cable 50A. Also, the O/E converter 53 is arranged on the input module 20 side of the optical fiber 52 in the first cable 50A, or in the input module 20.

The first cable 50A is connected at one end to the endoscope 10, so the thickness of the first cable 50A affects the ease with which the endoscope 10 can be maneuvered (the operability of the endoscope 10). The distance from the endoscope 10 to the input module 20 during general observation is longer than the distance from the input module 20 to the control module 30, i.e., the length of the first cable 50A is relatively long, so the effect that the thickness of the first cable 50A has on the ease with which the endoscope 10 can be maneuvered is relatively large.

At this time, if an attempt is made to realize high speed transmission corresponding to high pixelization of the image pickup portion 11 using a type of cable (cable X5) that transmits an image pickup signal via the metal wire 54, for the first cable 50A, the image pickup signal must be divided into multiple lines and transmitted using multiple signal lines. As a result, the diameter of the first cable 50A increases, so the maneuverability of the endoscope 10 ends up being reduced.

In contrast, by using a type of cable (cable X1 to X4) that transmits an image pickup signal via the optical fiber 52, for the first cable 50A, large volumes of data can be transmitted per unit time even with one or a few lines. As a result, the diameter of the first cable 50A can be smaller, so the maneuverability of the endoscope 10 can be improved.

Furthermore, the endoscope 10 may be connected to various types of control modules 30 in combination, but at this time, various types of input modules 20 must also be used. Even in this case, the detachable first cable 50A is used to connect the endoscope 10 to the input module 20, so wide compatibility can be ensured while realizing high speed transmission by optical signal, by using one of the cables X1 to X4 that is a suitable type for the first cable 50A.

Also, when using one of the cables X1 to X4 for the second cable 50B (with combination numbers (1) to (4), (6) to (9), (11) to (14), (16) to (19), and (21) to (24)), the second cable 50B includes the optical fiber 52. At this time, the E/O converter 51 is arranged in the input module 20, or on the input module 20 side of the optical fiber 52 in the second cable 50B. Also, the O/E converter 53 is arranged on the control module 30 side of the optical fiber 52 in the second cable 50B, or in the control module 30.

As described above, there are a variety of combinations of the endoscope 10 and the control module 30, but because the detachable second cable 50B is used to connect the input module 20 to the control module 30, wide compatibility can be ensured while realizing high speed transmission by optical signal, by using one of the cables X1 to X4 that is a suitable type for the second cable 50B.

In particular, when one of the cables X1 and X2 is used for the second cable 50B, equipment having a conventional configuration that inputs an electrical signal can be used as the control module 30, while realizing high speed transmission by optical signal. Also, when one of the cables X1 and X3 is used for the second cable 50B, equipment having a conventional configuration that outputs an electrical signal can be used as the input module 20, while realizing high speed transmission by optical signal.

Figure 9:
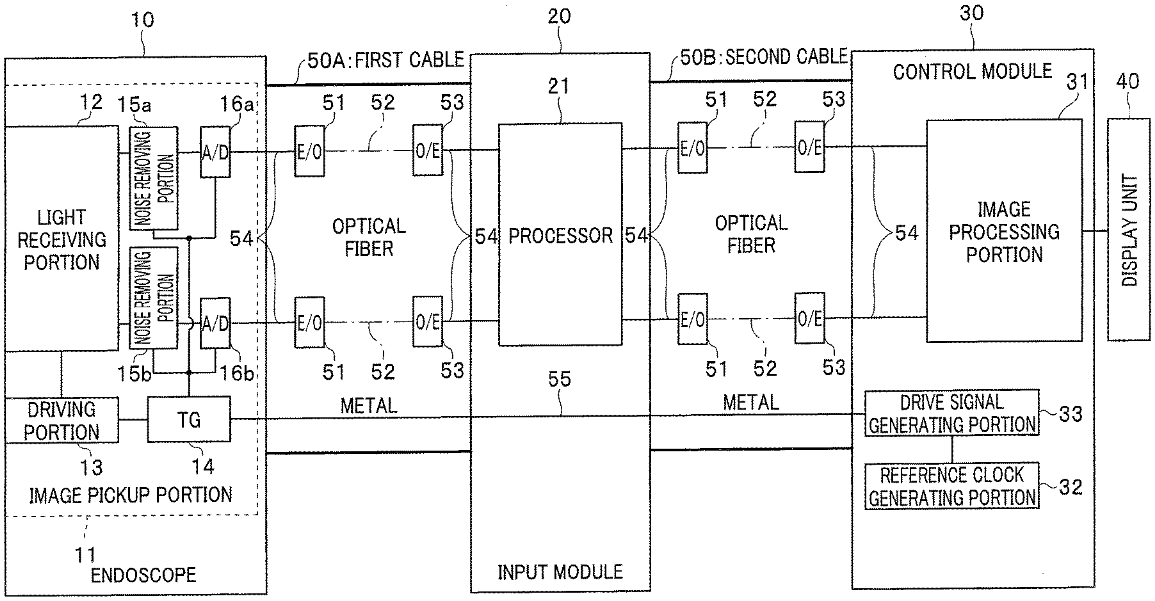
FIG. 9 is a view of a configuration example of an endoscope system according to the first embodiment.

FIG. 9 is a view of a configuration example of an endoscope system.

The example shown in FIG. 9 is a configuration indicated by combination number (13) in FIG. 8, in which the cable X1 is used for both the first cable 50A and the second cable 50B.

The image pickup portion 11 is an image pickup apparatus that picks up an image of a subject and outputs the image as, for example, a digital signal of a plurality of lines. The image pickup portion 11 includes a light receiving portion 12, a driving portion 13, a timing generator (TG) 14, noise removing portions 15*a* and 15*b*, and A/D converters 16*a* and 16*b*.

The light receiving portion 12 has a plurality of pixels to be photoelectrically converted that are two-dimensionally arranged. The light receiving portion 12 photoelectrically converts an optical image of a subject, which is formed by an objective optical system, not shown, and outputs an analog image pickup signal (electrical signal).

The driving portion 13 drives the light receiving portion 12 on the basis of a timing signal. The driving portion 13 is a drive circuit that performs control to start exposure by resetting the respective pixels arranged on the light receiving portion 12 and reading out a reset signal, and end exposure by reading out pixel signals for the respective pixels when a predetermined exposure time is reached.

The TG 14 generates a timing signal on the basis of a drive signal from a drive signal generating portion 33, described later, of the control module 30, and supplies the generated timing signal to respective circuits in the image pickup portion 11, e.g., the driving portion 13, the noise removing portions 15*a* and 15*b*, and the A/D converters 16*a* and 16*b*. Therefore, the respective circuits in the image pickup portion 11 work in cooperation on the basis of the timing signal.

The noise removing portion 15*a* removes noise from the image pickup signal from the image pickup area A1 in FIG. 2, for example, and the noise removing portion 15*b* removes noise from the image pickup signal from the image pickup area A2, for example. More specifically, the noise removing portions 15*a* and 15*b* remove reset noise by performing correlated double sampling in which the reset signal is subtracted from the pixel signal obtained by the exposure, on the respective pixel signals. Note that the noise removing portions 15*a* and 15*b* may of course also be configured to remove other noise.

The A/D converter 16*a* converts the analog image pickup signal outputted from the noise removing portion 15*a* into a digital image pickup signal (electrical signal), and the A/D converter 16*b* converts the analog image pickup signal outputted from the noise removing portion 15*b* into a digital image pickup signal (electrical signal).

The digital image pickup signals outputted from the A/D converters 16*a* and 16*b* are each transmitted to the E/O converter 51 of the first cable 50A via the metal wire 54.

Here, the endoscope 10 may be either a rigid endoscope or a flexible endoscope.

For example, when the endoscope 10 is configured as a rigid endoscope, the image pickup portion 11 is arranged in a camera head, and receives reflected light from the subject at a distal end of the rigid endoscope, transmits the light via an image guide fiber bundle, and performs photoelectric conversion with the image pickup portion 11 of the camera head. Also, when a configuration (the endoscope Al in FIG. 5) in which the endoscope 10 is provided with the E/O converter 51 is employed, the E/O converter 51 may also be arranged in the camera head.

On the other hand, when the endoscope 10 is configured as a flexible endoscope, the image pickup portion 11 is arranged in a distal end portion of an elongated insertion portion. Also, when a configuration (the endoscope A1 in FIG. 5) in which the endoscope 10 is provided with the E/O converter 51 is employed, the E/O converter 51 may also be arranged in the insertion portion, but from the viewpoint of reducing the diameter of the insertion portion, the E/O converter 51 is preferably arranged within an operation portion that operates the insertion portion.

The first cable 50A in the example shown in FIG. 9 includes the E/O converter 51, the optical fiber 52, and the O/E converter 53, and converts an image pickup signal into an optical signal by the E/O converter 51, transmits the converted optical signal with the optical fiber 52, converts the transmitted optical signal into an electrical signal by the O/E converter 53, and outputs the converted electrical signal to the input module 20 via the metal wire 54, for each line.

Continuing on, the input module 20 includes the processor 21 configured to perform the predetermined signal correction described above. Here, the predetermined signal correction performed by the processor 21 is processing that converts an image pickup signal that has a model dependency or an individual dependency received from the endoscope 10 into an image pickup signal with higher versatility. Note that while a case in which the processor 21 operates in accordance with a processing program for performing a predetermined signal correction is described below, the processor 21 is not prevented from being configured as a dedicated processing circuit that performs a predetermined signal correction. Note that when a configuration in which operation is performed in accordance with the processing program is employed, the processing content may be modified or new processing may be performed, by rewriting the processing program, as described in a second embodiment that will be described later.

Examples of the predetermined signal correction performed by the processor 21 include a correction based on correction information of an optical characteristic of the objective optical system of the endoscope 10, a pixel defect correction based on defective pixel information of the image pickup portion 11, a white balance correction based on white balance characteristic information of the image pickup portion 11, a color variation correction based on color variation correction information of the image pickup portion 11, and a conversion to a signal of a video format that is compatible with a signal processed by the control module 30 that is the destination. The processor 21 performs at least one of these types of processing, for example.

The input module 20 transmits the image pickup signal after processing to the E/O converter 51 of the second cable 50B, via the metal wire 54.

The second cable 50B in the example shown in FIG. 9 is provided with the E/O converter 51, the optical fiber 52, and the O/E converter 53, and converts an image pickup signal into an optical signal by the E/O converter 51, transmits the converted optical signal through the optical fiber 52, converts the transmitted optical signal into an electrical signal by the O/E converter 53, and outputs the converted electrical signal to the control module 30 via the metal wire 54, for each line.

Also, a plurality of the optical fibers 52 are disposed parallel to each other in the first and second cables 50A and 50B.

Note that the plurality of optical fibers 52 disposed in the first and second cables 50A and 50B are, for example, made of silica glass and formed with extremely small diameters (for example, diameters of 0.125 mm), and are thus extremely weak. Therefore, each of the optical fibers 52 is protected by being primarily coated with an ultraviolet curable resin, for example, and then being further covered by a protective tube, for example. At this time, the plurality of optical fibers 52 that have been primarily coated may be held together and covered by a protective tube, or each of the plurality of optical fibers 52 that have been primarily coated may be individually covered by a protective tube.

Also, a metal wire 55 disposed in the first and second cables 50A and 50B is typically configured by a plurality of wires, as will be described later. At this time, the plurality of wires may be covered individually by a protective tube, or two or more of the wires in an insulated state may be held together and protected by a single protective tube.

Also, the plurality of optical fibers 52 and the metal wire 55 that is a plurality of wires inside the first and second cables 50A and 50B may be suitably disposed. For example, the plurality of optical fibers 52 and the metal wire 55 that is a plurality of wires inside the first and second cables 50A and 50B may be disposed symmetrically with respect to the cable center axis. If an arrangement symmetrical to the cable center axis is adopted, the first and second cables 50A and 50B can be bent with the same curvature in an arbitrary direction, and thus a case in which the first and second cables 50A and 50B will bend easily in one specific direction and not bend easily in another specific direction will not occur. Accordingly, the first and second cables 50A and 50B can be easily maneuvered.

Examples of the arrangement symmetrical to the cable center axis include symmetrically disposing the metal wire 55 that is a plurality of wires such that the metal wire 55 is wound around the plurality of optical fibers 52, which are held together, with the plurality of optical fibers 52 as the axial center, or symmetrically disposing the plurality of optical fibers 52 such that the plurality of optical fibers 52 are wound around the metal wire 55, which is held together, with the metal wire 55 as the axial center. Whatever arrangement is adopted, the metal wire 55 can function as a tension member that protects the optical fibers 52 from tension applied to the first and second cables 50A and 50B.

The control module 30 includes an image processing portion 31, a reference clock generating portion 32, and a drive signal generating portion 33.

The image processing portion 31 is an image processing apparatus that performs various kinds of image processing on an image pickup signal with enhanced versatility that has been received from the input module 20, and generates a video signal.

More specifically, the image processing portion 31 combines the two lines of image pickup signals outputted from the O/E converter 53 (for example, an image pickup signal according to the image pickup area A1 and an image pickup signal according to the image pickup area A2), and configures a full screen image. Moreover, the image processing portion 31 performs typical image processing such as demosaicking processing, white balance processing, noise reduction processing, color matrix processing, and gamma conversion processing, on the integrated full screen image, and generates and outputs a video signal.

The reference clock generating portion 32 is a reference clock generating circuit that includes a crystal oscillator, for example, and generates a reference clock with a reference frequency.

The drive signal generating portion 33 is a drive signal generating circuit that generates a drive signal for driving the image pickup portion 11, on the basis of the reference clock generated by the reference clock generating portion 32. The metal wire 55 is arranged between the drive signal generating portion 33 and the TG 14 of the endoscope 10 via the second cable 50B, the input module 20, and the first cable 50A. The drive signal (electrical signal) generated by the drive signal generating portion 33 is transmitted to the TG 14 via the metal wire 55.

Therefore, not only the optical fiber 52 and the metal wire 54 that transmit image pickup signals, but also the metal wire 55 that is a metal transmitting member that transmits a control signal such as a drive signal, is arranged in the first and second cables 50A and 50B of the present embodiment. The metal wire 55 is typically configured by a plurality of wires, as described above, and includes a signal transmitting wire and a ground wire, for example.

Note that in the example shown in FIG. 9, the configuration is such that the TG 14 is arranged in the endoscope 10, and the reference clock generating portion 32 and the drive signal generating portion 33 are arranged in the control module 30 (the configuration of (5) in Table 1 below), but the configuration is not limited to this. Any one of the configurations in Table 1 below may be adopted. Here, in Table 1, only the reference numerals for the TG 14, the reference clock generating portion 32, and the drive signal generating portion 33 are listed.

TABLE 1

| | Endoscope | Input Module | Control Module |
|---|---|---|---|
| (1) | | | 14, 33, 32 |
| (2) | | 14 | 33, 32 |
| (3) | | 14, 33 | 32 |
| (4) | | 14, 33, 32 | |
| (5) | 14 | | 33, 32 |
| (6) | 14 | 33 | 32 |
| (7) | 14 | 33, 32 | |
| (8) | 14, 33 | | 32 |
| (9) | 14, 33 | 32 | |
| (10) | 14, 33, 32 | | |

Therefore, in a case where any one of the configurations (1) to (9) is adopted, the metal wire 55 transmits at least one of the reference clock, the drive signal, and the timing signal. On the other hand, when the configuration of (10) is adopted, the metal wire 55 itself need not be provided. Also, when any one of the configurations (4), (7), and (9) is adopted, the metal wire 55 need not be provided in the second cable 50B.

Note that with the configuration of (10), for example, the TG 14, the reference clock generating portion 32, and the drive signal generating portion 33 are arranged in the camera head when the endoscope 10 is configured as a rigid endoscope, and are arranged in the image pickup portion 11 of the distal end portion of the insertion portion or in the operation portion described above when the endoscope 10 is configured as a flexible endoscope. In particular, when the endoscope 10 is a flexible endoscope, a suitable split arrangement in which the TG 14 is disposed in the image pickup portion 11, and the reference clock generating portion 32 and the drive signal generating portion 33 are disposed in the operation portion, or in which the TG 14 and the drive signal generating portion 33 are disposed in the image pickup portion 11, and the reference clock generating portion 32 is disposed in the operation portion, for example, is possible. With the configurations of (8) and (9) as well, a split arrangement in which the TG 14 is disposed in the image pickup portion 11, and the drive signal generating portion 33 is disposed in the operation portion, is similarly possible.

A display unit 40 is configured having a monitor or the like, and observably displays the video signal generated by the image processing portion 31.

Figure 10:
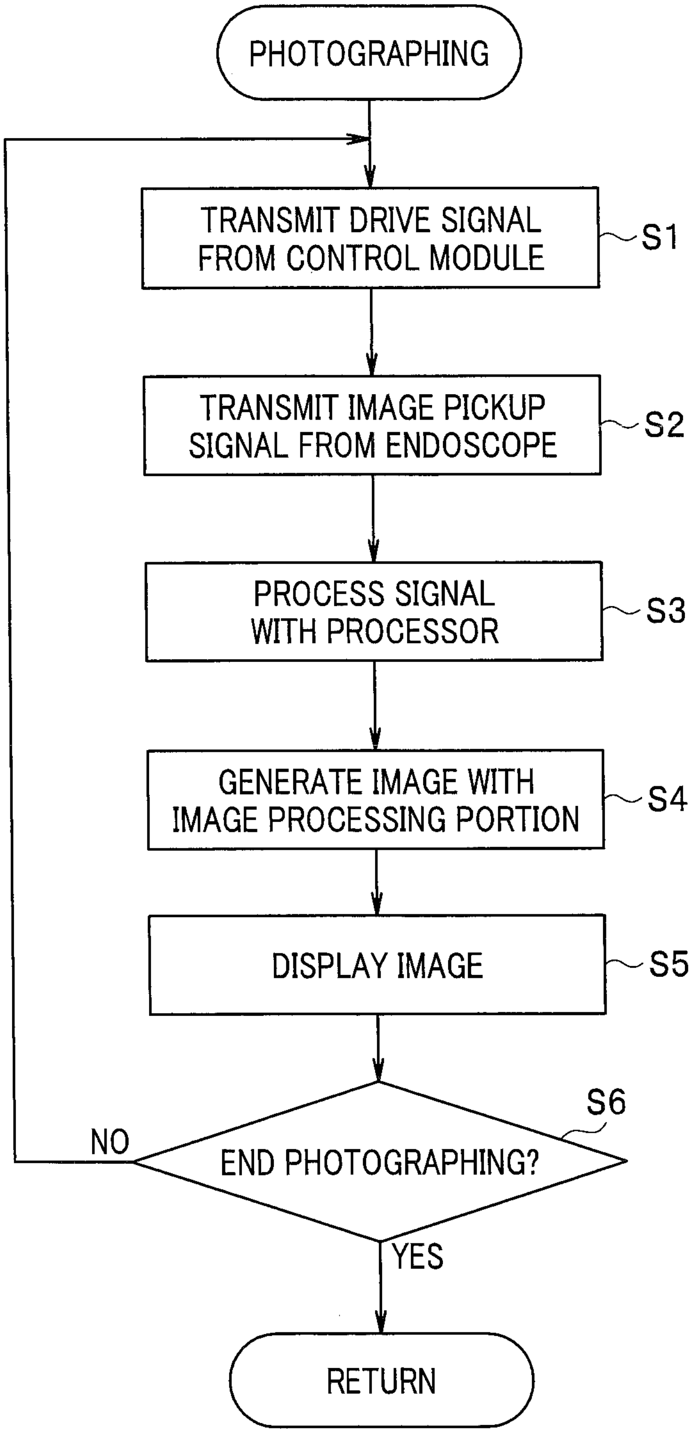
FIG. 10 is a flowchart illustrating a photographing process of the endoscope system according to the first embodiment.

Next, FIG. 10 is a flowchart illustrating a photographing process of an endoscope system.

When a power supply of an endoscope system is turned on and a main process (see FIG. 12, for example) is started, and there is a command to start photographing in the main process, the photographing process shown in FIG. 10 is started.

Then, the drive signal generating portion 33 generates a drive signal on the basis of a reference clock generated by the reference clock generating portion 32. The generated drive signal is transmitted from the control module 30 to the TG 14 of the endoscope 10 via the metal wire 55 (step S1).

The TG 14 generates a timing signal on the basis of the received drive signal, and supplies the generated timing signal to the respective circuits in the image pickup portion 11. The driving portion 13 controls the light receiving portion 12 to pick up an image and output an image pickup signal, on the basis of the received timing signal. Noise in the outputted image pickup signal is removed by the noise removing portions 15*a* and 15*b*, and the outputted image pickup signal is then converted into a digital signal by the A/D converters 16*a* and 16*b*, and transmitted from the image pickup portion 11 of the endoscope 10 to the processor 21 of the input module 20 via the first cable 50A (step S2).

The processor 21 performs a predetermined signal correction on the received image pickup signal, and transmits the image pickup signal after the correction to the image processing portion 31 of the control module 30 via the second cable 50B (step S3).

The image processing portion 31 performs image processing such as the image processing described above on the received image pickup signal, and generates a video signal (step S4).

The video signal generated by the image processing portion 31 is transmitted to the display unit 40, and a video is displayed on the display unit 40 (step S5).

Then, a control apparatus such as a CPU, not shown, in the control module 30, for example, determines whether to end photographing (step S6). If it is determined that photographing is not ended, the process returns to step Si described above.

On the other hand, if it is determined in step S7 that photographing is ended, the process returns from the photographing process to the main process.

According to this kind of first embodiment, the image pickup signal can be transmitted at high speed in at least one of between the image pickup portion 11 and the processor 21, and between the processor 21 and the image processing portion 31, because the electrical signal that is the image pickup signal is converted into an optical signal and transmitted.

Also, the endoscope 10 is connectable in a compatible manner to the control module 30 because the input module 20 that includes the processor 21 is disposed between the endoscope 10 and the control module 30. As a result, compatibility between the endoscope 10 and the control module 30 can be increased without making the configuration on the control module 30 side more complex.

Because the endoscope 10 and the input module 20 are connected by the first cable 50A, and the input module 20 and the control module 30 are connected by the second cable 50B, various types of endoscopes 10 and various types of control modules 30 can be connected in desirable combinations via an input module 20 that is suitable for the type of endoscope 10 and control module 30.

In a case where one of the cables X1 to X4 is used for the first cable 50A, the E/O converter 51 may be arranged either in the endoscope 10 or on the endoscope 10 side of the optical fiber 52 in the first cable 50A, and the O/E converter 53 may be arranged either on the input module 20 side of the optical fiber 52 in the first cable 50A or in the input module 20, so the degree of freedom in the arrangement increases.

Similarly, in a case where one of the cables X1 to X4 is used for the second cable 50B, the E/O converter 51 may be arranged either in the input module 20 or on the input module 20 side of the optical fiber 52 in the second cable 50B, and the O/E converter 53 may be arranged either on the control module 30 side of the optical fiber 52 in the second cable 50B or in the control module 30, so the degree of freedom in the arrangement increases.

Moreover, the processor 21 can reduce the model dependency or the individual dependency of the endoscope 10, and thus increase the versatility of the image pickup signal, by performing at least one of a correction based on correction information of an optical characteristic of the objective optical system of the endoscope 10, a pixel defect correction based on defective pixel information of the image pickup portion 11, a white balance correction based on white balance characteristic information of the image pickup portion 11, and a color variation correction based on color variation correction information of the image pickup portion 11.

Also, the processor 21 performs processing that converts the electrical signal into a signal of a video format that is compatible with the signal processed by the control module 30, as the predetermined signal correction. As a result, there is no longer a need for the control module 30 to correspond to a wide variety of video formats, which enables the configuration of the control module 30 to be simplified and the cost to be reduced.

Also, because a timing signal is transmitted to the driving portion 13, or a drive signal for generating a timing signal is transmitted to the image pickup portion 11, via the metal wire 55, the endoscope 10 no longer needs to be provided with the drive signal generating portion 33, or no longer needs to be provided with the TG 14 either, so the configuration of the endoscope 10 can be simplified, which contributes to a reduction in the weight and diameter of the endoscope 10.

[Second Embodiment]

Figure 11:
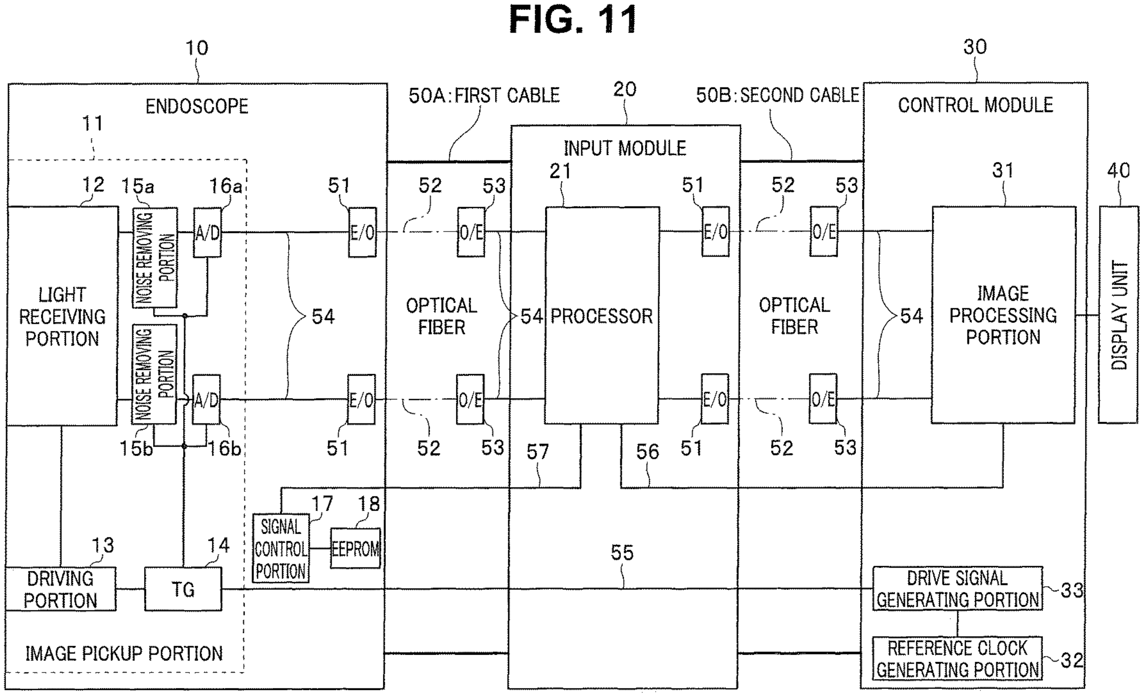
FIG. 11 is a view of a configuration example of an endoscope system according to a second embodiment of the present invention.
Figure 12:
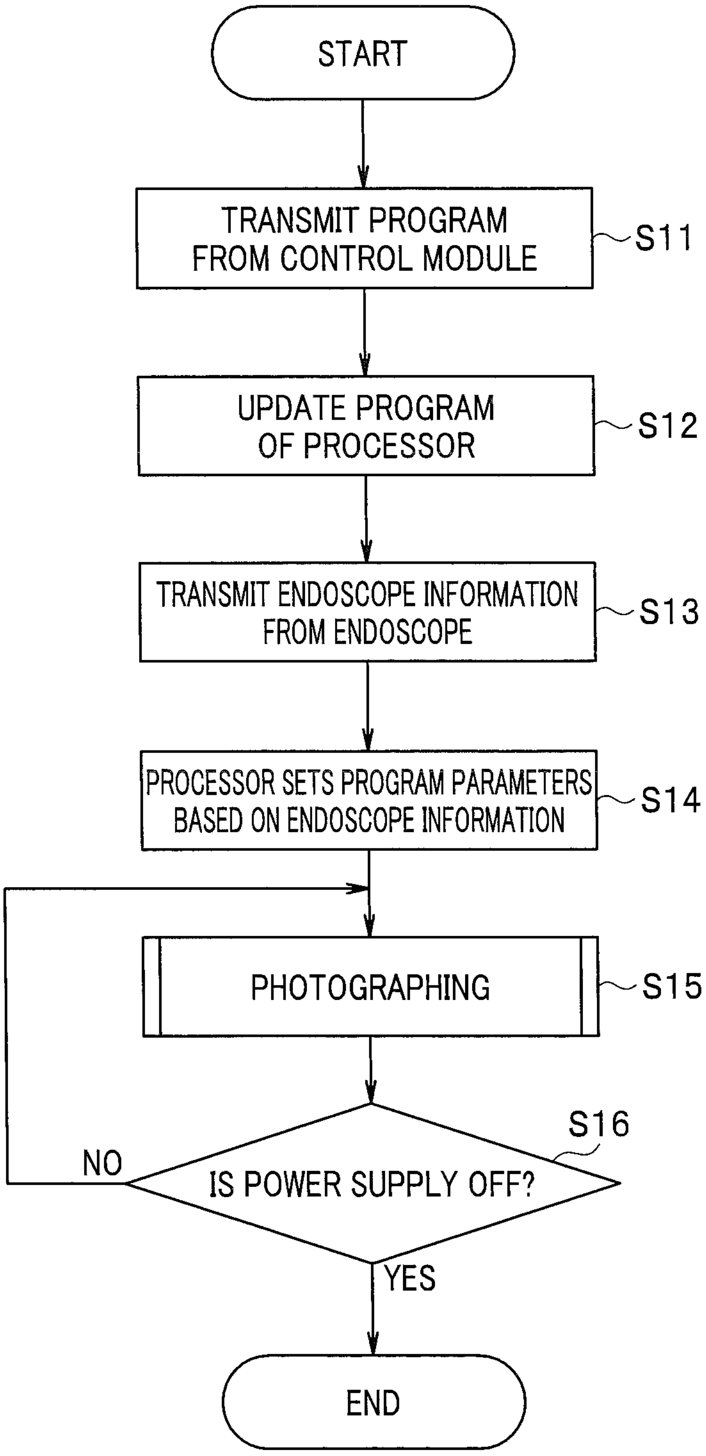
FIG. 12 is a flowchart illustrating operation of the endoscope system according to the second embodiment.

FIG. 11 and FIG. 12 are views illustrating a second embodiment of the present invention. FIG. 11 is a view of a configuration example of an endoscope system. In the second embodiment, portions similar to portions in the first embodiment described above will be denoted by the same reference numerals, and descriptions of these portions will be omitted as appropriate. Mainly only points that differ will be described.

The present embodiment is configured such that, in addition to the first embodiment described above, the processing program to be executed by the processor 21 may be modified.

Note that the example shown in FIG. 11 is the configuration indicated by combination number (1) in FIG. 8, in which the cable X2 is used for both the first cable 50A and the second cable 50B.

The endoscope 10 includes the image pickup portion 11 described above, as well as a signal control portion 17, EEPROM 18, and an E/O converter 51 for each line.

Also, the input module 20 includes the processor 21 described above, as well as an E/O converter 51 on the downstream side of the processor 21.

Also, the image processing portion 31 and the processor 21 are connected so as to enable electrical communication via a metal wire 56 included in the second cable 50B, and the signal control portion 17 and the processor 21 are connected so as to enable electrical communication via a metal wire 57 included in the first cable 50A.

The signal control portion 17 is a signal control circuit that performs control that reads out endoscope information stored in the EEPROM 18, and transmits the endoscope information to the processor 21 of the input module 20 via the metal wire 57.

The EEPROM 18 is a storage device that stores endoscope information (various kinds of information concerning the endoscope 10) in a non-volatile manner The EEPROM 18 stores, as the endoscope information, at least one of correction information of an optical characteristic of the objective optical system, defective pixel information of the image pickup portion 11, white balance characteristic information of the image pickup portion 11, and color variation correction information of the image pickup portion 11, for example. Further, the EEPROM 18 also stores the serial number of the endoscope 10 as the endoscope information.

Also, the processor 21 performs, as a predetermined signal correction with the endoscope information as a parameter, at least one of a correction based on the correction information of an optical characteristic of the objective optical system of the endoscope 10, a pixel defect correction based on the defective pixel information of the image pickup portion 11, a white balance correction based on the white balance characteristic information of the image pickup portion 11, and a color variation correction based on the color variation correction information of the image pickup portion 11.

The E/O converter 51 provided for each line in the endoscope 10 converts the inputted electrical signal into an optical signal and outputs the optical signal, as described above.

Next, FIG. 12 is a flowchart illustrating operation of the endoscope system.

FIG. 12 mainly lists processes related to transmitting a processing program and the like to the processor 21 of the input module 20 in the main process executed when the power supply of the endoscope system is turned on. Descriptions of the other processes are omitted.

When the power supply of the endoscope system is turned on and the process is started, the control module 30 transmits a processing program (a processing program for performing a predetermined signal correction) executed by the processor 21 of the input module 20 to the processor 21 via the metal wire 56 (step S11).

Note that in the configuration example shown in FIG. 11, it is presupposed that the image processing portion 31 stores the processing program, and the image processing portion 31 transmits the processing program, but the present invention is not limited to this. For example, a separate storage device may be provided inside the control module 30, and a control apparatus such as a CPU in the control module 30 may read out the processing program from the storage device and transmit the processing program.

The processor 21 updates the existing processing program with the processing program received from the image processing portion 31 (step S12). As a result, the processor 21 is able to execute the latest processing program. Note that the entire processing program does not need to be transmitted or updated. Only a portion of the processing program may be transmitted and updated.

Also, the signal control portion 17 of the endoscope 10 reads out the endoscope information from the EEPROM 18 and transmits the read-out endoscope information to the processor 21 via the metal wire 57 before the image pickup portion 11 outputs the image pickup signal that is an electrical signal (step S13).

The processor 21 sets program parameters necessary when executing the processing program on the basis of the endoscope information received from the signal control portion 17 (step S14). As a result, the processor 21 is able to execute the processing program and perform the predetermined signal correction with parameters suitable for the configuration of the endoscope 10.

However, if the processor 21 is unable to acquire the endoscope information from the endoscope 10, such as when the endoscope 10 is a type that does not transmit endoscope information, the processor 21 is able to execute the processing program on the basis of specified parameters.

In this way, the photographing process shown in FIG. 10 of the first embodiment described above is executed after preparation for executing the processing program by the processor 21 has been completed (step S15). As a result, the processor 21 performs the predetermined signal correction with the processing program, with the endoscope information as the parameters, in step S3 of FIG. 10.

Then, it is determined whether a command to turn off the power supply of the endoscope system according to operation of a power supply switch, for example, has been inputted (step S16). If the command has not been inputted, the photographing process of step S15 is repeatedly executed. If the command has been inputted, this process ends.

Note that in the process shown in FIG. 12 it is presumed that the control module 30 transmits the processing program to the processor 21, and the signal control portion 17 transmits the endoscope information to the processor 21, as an automatic process when the power supply of the endoscope system is turned on. However, the present invention is not limited to this. The respective processes may be performed in response to receiving a command from a user, or the parameters may be set on the basis of input from the user.

Also, in the description above, the processing program is transmitted from the control module 30 to the processor 21, but instead, the processing program may be transmitted from the endoscope 10 to the processor 21.

In this case, the EEPROM 18 stores the processing program for performing the predetermined signal correction, and the signal control portion 17 reads out the processing program stored in the EEPROM 18, and transmits the processing program that has been read out to the processor 21 via the metal wire 57. At this time, if the processing program stored in the EEPROM 18 is a program according to the endoscope information, a process to transmit the endoscope information separate from the processing program is not necessary. In this way, the processor 21 performs the predetermined signal correction with the processing program transmitted from the signal control portion 17.

This kind of second embodiment displays almost the same effects as the first embodiment described above. Also, the control module 30 transmits the processing program for performing the predetermined signal correction to the processor 21, so the processor 21 is able to execute the latest processing program.

Also, the signal control portion 17 transmits the endoscope information read out from the EEPROM 18 to the processor 21 before the image pickup portion 11 outputs the electrical signal, so a signal correction suitable for the configuration of the endoscope 10 can be performed.

Also, the processing program and the endoscope information are transmitted via a dedicated metal wire, so transmission of the image pickup signal will not be affected.

Furthermore, the processing program and the endoscope information are transmitted to the processor 21 as an automatic process when the power supply of the endoscope system is turned on, so the latest process when endoscope system is used can be performed without placing a burden on the user.

In addition, the processor 21 sets the parameters for performing the predetermined signal correction on the basis of the endoscope information stored in the EEPROM 18 provided in the endoscope 10, so endoscope information that matches the endoscope 10 can be without fail acquired just by connecting the endoscope 10.

Also, the processor 21 is able to execute the latest processing program suitable for the endoscope 10 also by the signal control portion 17 of the endoscope 10 reading out the processing program stored in the EEPROM 18 and transmitting the processing program to the processor 21.

Note that the respective portions described above may also be configured as circuits. Also, if an arbitrary circuit can perform the same function, the arbitrary circuit may be implemented as a single circuit or as a combination of a plurality of circuits. Furthermore, an arbitrary circuit is not limited to being configured as a dedicated circuit for performing a target function, and may be configured to perform a target function by causing a general purpose circuit to execute a processing program.

Also, in the description above, mainly an endoscope system is described, but the present invention may also be an operation method that causes an endoscope system to operate in the manner described above, a processing program for causing a computer to perform processing similar to the processing of the endoscope system, or a non-transitory storage medium that is readable by a computer on which the processing program is stored, or the like.

Furthermore, the present invention is not limited to the embodiments described above, and may be embodied by modifying the constituent elements in the implementation phase without departing from the scope of the present invention. Also, various aspects of the invention may be formed by suitable combinations of a plurality of constituent elements disclosed in the embodiments. For example, several constituent elements may be omitted from all of the constituent elements illustrated in the embodiments. Furthermore, constituent elements across different embodiments may be suitably combined. In this way, various modifications and applications are of course possible without departing from the scope of the invention.

What is claimed is:

1. An endoscope system comprising:

an endoscope comprising an image pickup sensor configured to pick up an image of a subject and output the image as an electrical signal;

an electrical-to-optical converter configured to convert the electrical signal into an optical signal;

a first cable comprising an optical transmitting member configured to transmit the optical signal;

an optical-to-electrical converter configured to convert the optical signal transmitted by the optical transmitting member into the electrical signal;

an input module connected to the endoscope via the first cable, wherein the input module comprises a processor comprising hardware, the processor being configured to perform, as a predetermined signal correction, processing that converts the electrical signal from the optical-to-electrical converter into a modified electrical signal having a video format that is compatible with a processing performed by an image processor comprising hardware, and output the modified electrical signal;

a second cable configured to transmit the modified electrical signal to the image processor; and a control module connected to the input module via the second cable, wherein the control module comprises the image processor comprising hardware, wherein the image processor is configured to perform image processing on the modified electrical signal to generate a video signal, wherein:

the second cable comprises a metal transmitting member;

the control module is configured to transmit a processing program for performing the predetermined signal correction to the processor via the metal transmitting member of the second cable; and the processor is configured to perform the predetermined signal correction with the processing program, and wherein:

the first cable further comprises a second metal transmitting member;

the endoscope further comprises:

a memory configured to store endoscope information; and a signal control circuit configured to:

read out the endoscope information stored in the memory; and transmit the endoscope information read out from the memory to the processor via the second metal transmitting member of the first cable before the image pickup sensor outputs the electrical signal; and the processor is configured to perform the predetermined signal correction with the processing program with the endoscope information as a parameter.

2. The endoscope system according to claim 1, wherein:

the electrical-to-optical converter is arranged in the endoscope, or on an endoscope side of the optical transmitting member in the first cable; and the optical-to-electrical converter is arranged on an input module side of the optical transmitting member in the first cable, or in the input module.

3. The endoscope system according to claim 1, wherein the second cable comprises a second optical transmitting member configured to transmit an optical signal, wherein the endoscope system further comprises:

a second electrical-to-optical converter arranged in one of the input module, or on an input module side of the second optical transmitting member in the second cable; and a second optical-to-electrical converter arranged on one of a control module side of the second optical transmitting member in the second cable, or in the control module, and wherein:

the second electrical-to-optical converter is configured to convert the modified electrical signal to an optical signal;

the second optical transmitting member is configured to transmit the optical signal converted from the modified electrical signal; and the second optical-to-electrical converter is configured to convert the optical signal transmitted by the second optical transmitting member to the modified electrical signal.

4. The endoscope system according to claim 1, wherein:

the image processor is configured to transmit the processing program to the processor, and the signal control circuit is configured to transmit the endoscope information to the processor as an automatic process when a power supply of the endoscope system is turned on.

5. The endoscope system according to claim 1, wherein:

the memory is configured to store, as the endoscope information, at least one of correction information of an optical characteristic of an objective optical system of the endoscope, defective pixel information of the image pickup sensor, white balance characteristic information of the image pickup sensor, and color variation correction information of the image pickup sensor; and the processor is configured to perform, as the predetermined signal correction with the endoscope information as the parameter, at least one of a correction based on the correction information of the optical characteristic of the objective optical system of the endoscope, a pixel defect correction based on the defective pixel information of the image pickup sensor, a white balance correction based on the white balance characteristic information of the image pickup sensor portion, and a color variation correction based on the color variation correction information of the image pickup sensor.

6. The endoscope system according to claim 1, wherein:

the image pickup sensor comprises:

a plurality of pixels configured to receive reflected light from the subject and perform optical-to-electrical conversion; and a drive circuit configured to drive the plurality of pixels on the basis of a timing signal; and the endoscope is configured to transmit, via the second metal transmitting member of the first cable, at least one of the timing signal, a drive signal for generating the timing signal, and a reference clock for generating the drive signal, to the input module.

7. The endoscope system according to claim 1, wherein:

the image pickup sensor comprises:

a plurality of pixels configured to receive reflected light from the subject and perform optical-to-electrical conversion; and a drive circuit configured to drive the plurality of pixels on the basis of a timing signal;

the endoscope further comprises a reference clock generating circuit, a drive signal generating circuit, and a timing generator;

the reference clock generating circuit is configured to generate a reference clock;

the drive signal generating circuit is configured to:

receive the reference clock; and generate a drive signal based on the reference clock; and the timing generator is configured to receive the drive signal and generate the timing signal based on the drive signal.

8. An endoscope system comprising:

an endoscope comprising an image pickup sensor configured to pick up an image of a subject and output the image as an electrical signal;

an electrical-to-optical converter configured to convert the electrical signal into an optical signal;

a first cable comprising an optical transmitting member configured to transmit the optical signal;

an optical-to-electrical converter configured to convert the optical signal transmitted by the optical transmitting member into the electrical signal;

an input module connected to the endoscope via the first cable, wherein the input module comprises a processor comprising hardware, the processor being configured to perform, as a predetermined signal correction, processing that converts the electrical signal from the optical-to-electrical converter into a modified electrical signal having a video format that is compatible with a processing performed by an image processor comprising hardware, and output the modified electrical signal;

a second cable configured to transmit the modified electrical signal to the image processor; and a control module connected to the input module via the second cable, wherein the control module comprises the image processor comprising hardware, wherein the image processor is configured to perform image processing on the modified electrical signal to generate a video signal, wherein:

the first cable further comprises a metal transmitting member;

the endoscope further comprises:

a memory configured to store a processing program for performing the predetermined signal correction; and a signal control circuit configured to:

read out the processing program stored in the memory; and transmit the processing program read out from the memory to the processor via the metal transmitting member; and the processor is configured to perform the predetermined signal correction with the processing program.

* * * * *